US006010700A

United States Patent [19]

Richt

[11] Patent Number: 6,010,700
[45] Date of Patent: Jan. 4, 2000

[54] POLYPEPTIDES P57 OR P9.5 OF BORNA DISEASE VIRUS AND THEIR USE FOR DIAGNOSIS AND IMMUNIZATION

[76] Inventor: Jürgen A. Richt, Blauäckerweg 7 B, D-35248 Langgöns-Niederkleen, Germany

[21] Appl. No.: 08/803,603

[22] Filed: Feb. 21, 1997

[30] Foreign Application Priority Data

Feb. 21, 1996 [EP] European Pat. Off. .............. 96102575

[51] Int. Cl.[7] ............................ A61K 39/12; C12Q 1/70; C07K 14/08; C12N 7/00

[52] U.S. Cl. ........................... 424/186.1; 435/5; 435/7.1; 435/975; 435/235.1; 530/350; 930/220; 424/204.1

[58] Field of Search ............................. 424/186.1, 204.1, 424/224.1; 435/5, 235.1, 7.1, 975; 530/350; 930/220

[56] References Cited

PUBLICATIONS

Briese, T. et al. Proceedings of the National Academy of Sciences USA, vol. 91, pp. 4362–4366, May 1994.

Cubitt, B. et al. Journal of Virology, vol. 68, pp. 1382–1396, Mar. 1994.

De la Torre, J.C. Journal of Virology, vol. 68, pp. 7669–7675, Dec. 1994.

Murphy, B. R. et al. "Immunization Against Viruses." In: Virology, ed. B. N. Fields et al, Raven Press, NY, 1985.

*Primary Examiner*—Mary E. Mosher
*Attorney, Agent, or Firm*—Fulbright & Jaworski, LLP

[57] ABSTRACT

The invention involves polypeptides which correspond to amino acid sequences of protein p57 or protein p9.5 of Borna disease virus. These polypeptides, as well as DNA and RNA fragments are used in test kits and vaccines.

13 Claims, 2 Drawing Sheets

POLYPEPTIDES P57 OR P9.5 OF BORNA DISEASE VIRUS AND THEIR USE FOR DIAGNOSIS AND IMMUNIZATION

FIELD OF THE INVENTION

The present invention relates to the diagnosis and treatment of a viral infection caused by the Borna disease virus.

BACKGROUND AND PRIOR ART

Borna disease virus (BDV) is a neurotropic virus that causes an immune-mediated syndrome resulting in disturbances in movement and behaviour. Originally the disease was described as a natural infection of horses in a small city, Borna, in Southeast Germany.

Borna disease (BD) is an infectious disease of the central nervous system characterized by profound behavioural abnormalities, inflammatory cell infiltrates and the accumulation of disease-specific antigens in limbic system neurons. Naturally occurring infections with Borna disease virus (BVD), the etiological agent of Borna disease, have been confirmed mainly in horses and sheep. The disease can, however, be experimentally transmitted to a wide range of animal species including rodents and nonhuman primates with variable clinical and pathological manifestations. Recent epidemiological data suggest that Borna disease may be more widespread in a subclinical form. It is possible that Borna disease virus is involved in human disorders of the central nervous system. Therefore, it is important to have a reliable diagnostic test system and an effective treatment.

Borna disease virus has not been fully characterized yet, however, the genome of cell adapted Borna disease virus (BDV)-strains have been cloned and sequenced by Cubitt et al. [J. Virol. 68, p. 1382–1396 (1994)] and Briese et al. [Proc. Natl. Acad. Sci., USA, vol. 91, p. 4362–4366 (May 1994)].

BDV contains a nonsegmented negative-sense 8.9 kb RNA-genome with complementary 3' and 5' termini. Subgenomic RNAs have been mapped to the viral genome and some of them found to undergo posttranscriptional modification by RNA splicing. The features known up to now seem to indicate that BDV represents the prototype of a new group of animal viruses within the order Mononegavirales.

BDV is strictly neurotropic and disseminates by intraaxonal transport from the site of infection. The virus replicates in vitro in embryonic brain cells of various animal species. Cocultivation of such brain cells with various permanent cell lines such as MDCK or Vero cells results in a persistent infection. Infectivity is mainly cell associated, the virus is noncytopathic and spreads by cell to cell contact. Intracellular viral antigen can be demonstrated in the cell nucleus and cytoplasm of infected cells. Morphologically the virion appears to be a 60–90 nm enveloped, spherical particle containing an electron dense internal structure.

BDV replication in cells is associated with the presence of at least three virus-specific antigens with molecular weight of 18 (gp18), 24 (p24) and 38/40 (p38 or p40) kilodaltons. An enzyme-linked immunosorbent assay for detecting antibodies to Borna disease virus specific proteins is described by Briese et al. (Journal of Clinical Microbiology, 33, p. 348–351 (February 1995)]. The ELISA test described by Briese uses the proteins p38/40, p23 and gp18 which are found in vitro and in vivo in the nucleus and cytoplasm of infected cells. The recombinant proteins used in the ELISA assay of Briese were produced by using a cell-adapted laboratory BDV strain from persistently BDV-infected MDCK cells.

The disadvantage of the known ELISA test is that only a few BDV proteins are used and therefore not all infections of Borna disease virus can be reliably detected.

SUMMARY OF THE INVENTION

In the course of the present invention it has been found that polypeptides corresponding to the proteins p57 and p9.5, respectively, allow a better diagnosis of BDV infection and can be advantageously used for the preparation of vaccines.

The present invention relates therefore to polypeptides corresponding to the amino acid sequence of the protein p57 or p9.5 encoded by the Borna disease virus having a sequence of at least 10 consecutive amino acids of the amino acid sequence given in FIG. 1 or FIG. 2, respectively.

From the prior art it was not clear whether the proteins p9.5 and p57 do in fact exist or whether they are only hypothetical proteins which are not produced in natural infections with BDV. Neither Briese et al. nor Cubitt et al. confirmed the expression of p57 or p9.5 or provided the isolated proteins.

In the course of the present invention it was found that the protein p9.5 is in fact produced and that this protein which is not glycosylated is located in the nucleus of infected MDCK cells. The protein p57 apparently is a glycosylated protein and the major BDV-specific surface protein which occurs not only in the cytoplasm of infected cells but also in their cell membrane probably determining the tropism of BDV by binding to the respective virus-specific cell receptor. The protein p57 probably also functions as a fusion protein i.e., a protein which causes the fusion of an infected cell with another uninfected cell. Such fusions allow the spread of the virus from cell to cell. Therefore, this protein is, from the therapeutic point of view extremely important, since a humoral or cell-mediated immune response directed against such a surface protein with fusion activity can be used for the preparation of an effective vaccine. Probably the protein p57 is modified after the translation by a protease like subtilisin or a furin protease which converts the p57 protein to the active form.

There is another advantage of the polypeptides according to the present invention. Since the sequences of the present invention were obtained from a field isolate of Borna disease virus (from horse), no modifications caused by the permanent culture of the laboratory strain occurred. The sequences of the claimed polypeptide p57 and of p9.5 differ therefore from the corresponding sequence described in the prior art.

The protein p9.5 occurs in the nucleus of persistently BDV-infected MDCK cells and is probably associated with the nucleic acid of the virus. Therefore, this protein can be advantageously used for the preparation of genomic viral RNA by selectively binding the protein p9.5 to a solid phase. This can be achieved by using affinity chromatography with specific antibodies directed against protein 9.5.

In a preferred embodiment of the present invention the polypeptides comprise the main epitope or main epitopes against which antibodies are formed. Therefore, the polypeptides preferably, have a length of at least 25 consecutive amino acids and more preferably of at least 50 consecutive amino acids of the amino acid sequence given in SEQ ID NO: 1 or SEQ NO: 2, respectively.

On the other hand the polypeptides according to the invention preferably, have an upper limit of not more than 80 consecutive amino acids of the amino acid sequence given in FIG. 1 or FIG. 2, respectively.

The present invention also concerns test kits for the determination of antibodies directed against Borna disease virus in a sample comprising at least one polypeptide according to the present invention and a label for the detection of the complex formed by the polypeptide and the antibodies to be determined.

The test kits are generally based on the detection of a complex formed by the polypeptide comprising at least one epitope and antibodies directed against said epitope. There are various forms of such test kits whereby the ELISA test is one of the most commonly used tests, because such a test can easily be handled by laboratories. In a preferred embodiment the polypeptide is linked to the surface of the wells of microtiter plates. The sample to be tested which is preferably a serum sample of the individual to be tested is brought into the well and removed after a definite period of time. Afterwards the well is washed and antibodies binding specifically to the polypeptide can be visualized by adding another antibody which specifically binds to the antibody remaining in the well. Said second antibody is usually covalently bound to a label which allows the detection of the complex formed within the test well. Such a label can preferably be selected from enzymes catalyzing a colour reaction as for example horseradish peroxidase.

In preferred embodiments of the present invention the test kits comprise the components for performing an ELISA, Western blot, RIA or dot blot test.

The method according to the invention for determining an infection by Borna disease virus comprises a) contacting a sample to be determined with at least one polypeptide according to the invention whereby the poly-peptide binds to antibodies elicited by a former infection of Borna disease virus and b) determining the binding of said polypeptide to the specific antibodies which are present in the sample to be tested.

In a further aspect the present invention concerns isolated DNA fragments which encode a polypeptide according to the invention whereby the DNA fragment is preferably not longer than 240 base pairs and more preferably not longer than 150 base pairs.

A further aspect of the present invention concerns isolated RNA fragments which encode a polypeptide according to the invention whereby the RNA fragment is not longer than 240 base pairs.

In preferred embodiments of the present invention the DNA and RNA fragments, respectively, have a sequence which corresponds at least partially to the sequences given in SEQ ID NOS: 4 and 5, respectively, or are complementary thereto.

The polypeptides according to the present invention can be used for the production of a vaccine.

The use of proteins, peptides and polypeptides for vaccination has been well-known for a long time. The methods of preparing the vaccine are well-known to those skilled in the art.

There is, however, a further technique for vaccination which can be performed with the nucleic acid fragments of the present invention. It has recently been found that plasmid DNA can be taken up by skeletal muscle cells in vivo without any special delivery mechanism and persist long-term in an extra-chromosomal, nonreplicative circular form. Thus foreign genes can be expressed transiently in skeletal muscle. It is also possible to include the DNA or RNA fragments of the present invention in infectious suicide virus particles which can be used directly for immunization. Furthermore it is also possible to inject the isolated DNA and RNA fragments, respectively, into the muscle of the human or animal to be immunized.

Depending upon the form of the DNA fragment to be used and how it is to be immunized the isolated DNA fragment can further comprise the sequences required for regulation of transcription and expression of the DNA fragment. If the nucleic acid is introduced in a vector, the nucleic acid fragment will be linked to suitable viral vectors or recombinant plasmids.

The DNA fragments and RNA fragments according to the present invention can therefore be used for nucleic acid immunization.

DETAILED DESCRIPTION OF PREFERRED EMBODIMENTS

EXAMPLE 1

Figure 1:
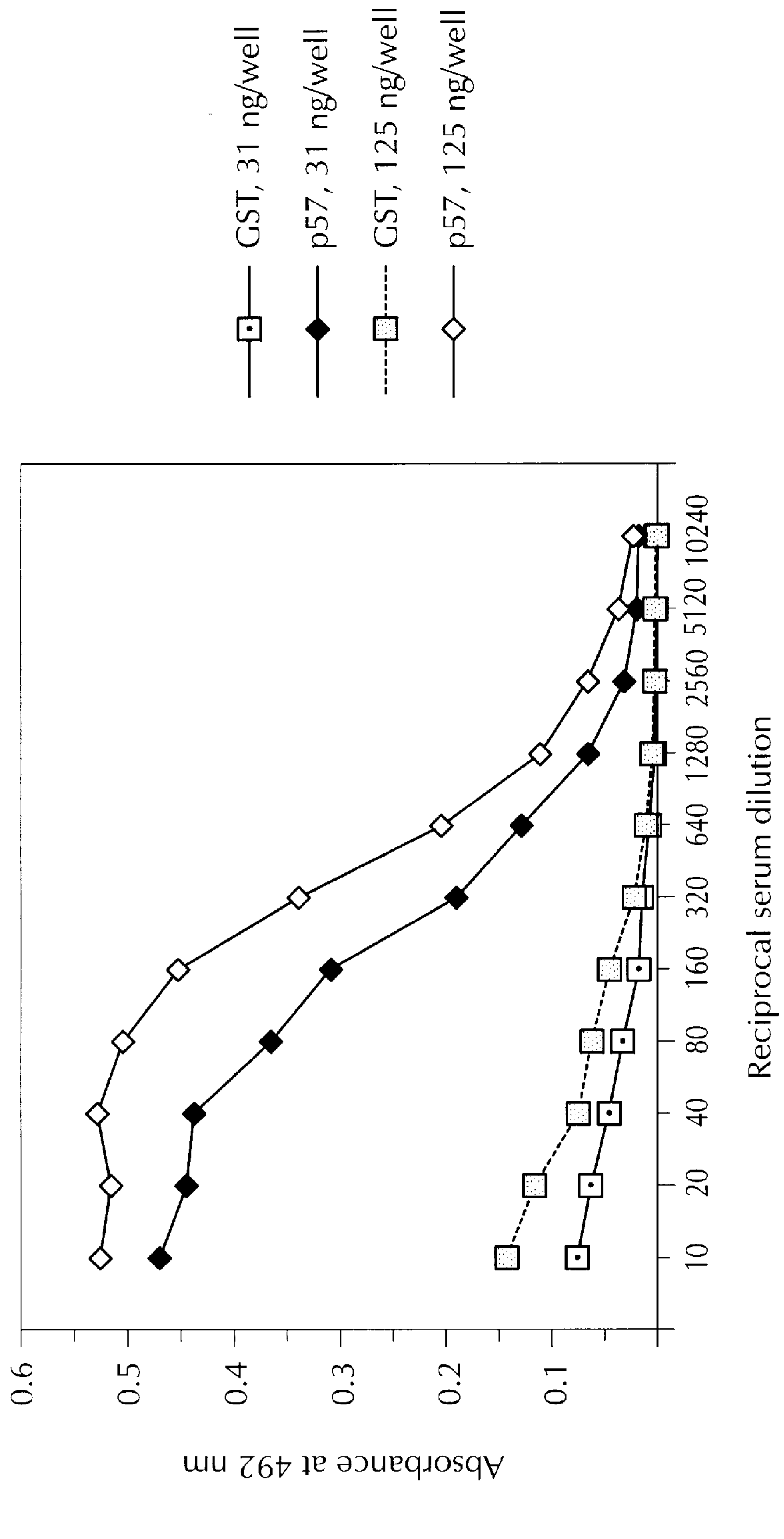
FIG. 1 shows the results obtained by the ELISA test as described in example 4.
Figure 2:
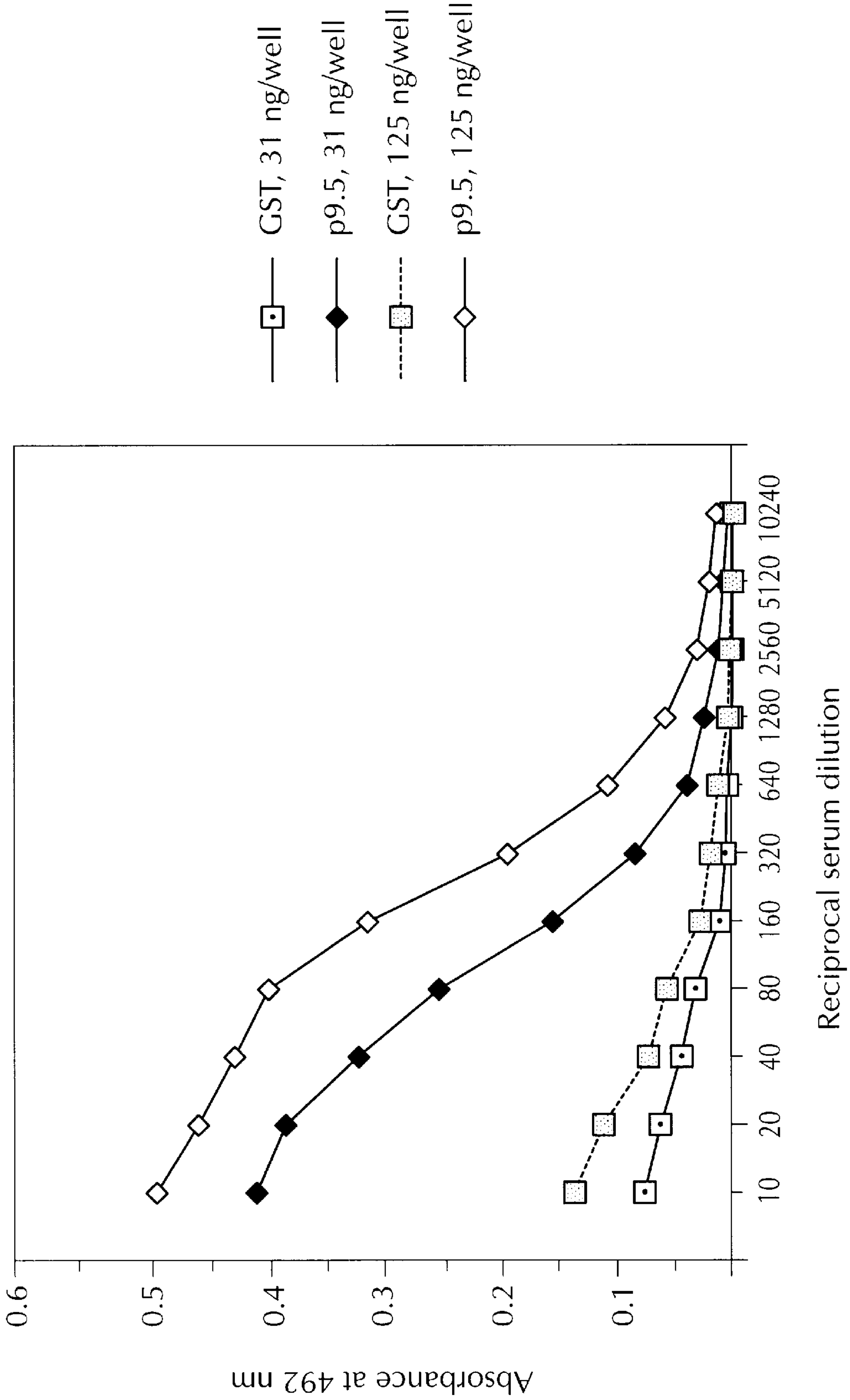
FIG. 2 shows the results obtained by the ELISA test as described in example 10.

Cloning and expression of the p57 and p47/c BDV-gene

The entire and the C-terminal region of the open reading frame of the p57 BDV-protein [p57/c; bp 2685-bp 3747, Cubitt et al., (1994) J. Virol. 68, 7669–7675, Briese et al. (1994) p57 bp x—3747] was amplified from RNA isolated from BDV-infected rats using the following primers:

```
C-terminal region:
3' Primer (anti-sense) GTAGAATTC TTATTCCTGCCACCGGCCGAGGCGTC SEQ ID NO: 6
entire p57 ORF:
5' Primer (sense): GATGGATCC ATGTACTGCAGTTTCGCGGACTGTAG     SEQ ID NO: 7
```

5'-Primer:

RNA was isolated from BDV-infected rat brain using the standard acid guanidium isothiocyanate-phenol-chloroform method and 2 pg RNA was used for RT-reaction. The conditions for the RT-reaction and the PCR were described by Richt et al., [Med. Microbiol. Immunol. 182 (1993) S. 293–304].

The amplified product was purified from agarose gels and cloned into the plasmid vector pGEX-2T (Pharmacia, #27-4801-01) after the restriction sites were cleaved using the restriction enzymes BamHI and EcoRI (Promega, Madison, USA). The viral gene was fused to the glutathion-S-transferase (GST) gene of *Schistosoma japonicum* controlled by the tac promotor. The expression plasmid was transformed into competent *E. coli* Sure™-cells. Recombinant plasmids were analyzed using restriction analysis and DNA-sequencing methods. The amino acid sequence of the fragment p57c deduced from the sequenced DNA fragment is shown in FIG. 3 (SEQ ID NO: 3).

EXAMPLE 2

Expression and purification of the p57 and p57/c BDV-proteins in *E. coli:*

100 ml of pGEX-p57/c containing *E. coli* were grown overnight in LB-medium with 0.1 mg/ml ampicillin (Serva, Heidelberg). This overnight culture was diluted in 1 liter of LB-medium with ampicillin and grown to log phase for 2–4 hours. The expression of the GST-p57/c and GST-p57 fusion proteins were induced with IPTG (0.1 nM; Promega, Heidelberg, Germany) for 4 hours. The bacteria were pelleted by centrifugation (5900 g, 10 min, 4° C.) and resuspended in PBS. The cells were lysed by sonication on ice and the cell debris pelleted by centrifugation (9800 rpm, 10 min, 4° C.). The sonicated fusion protein supernatants were added to an affinity matrix with Glutathione (Glutathione Sepharose 4 B; Pharmacia, Nr. 27-4570-01). The purification of the GST-p57/c and GST-p57 fusion proteins using Glutathione Sepharose 4B was done according to the protocol of the manufacturer. The eluted fusion proteins were dialyzed against 1× PBS for 24 hours at 4° C. The expression product was analyzed in SDS-PAGE and Immunoblot assays.

The expression of the virus-specific GST-p57/c and GST-p57 fusion protein by recombinant pGEX-p.57/c or pGEX-p57 clones were analyzed by immunoblotting using *E.coli* lysates treated with and without IPTG. As a control an *E.coli* lysate transformed with the nonrecombinant pGEX-2T plasmid was used. The quality of the eluted fusion protein was then analyzed in Western blot analyses using BDV-specific rat and rabbit antisera. The purified GST-p57/c as well as GST-p57 were easily detected by virus-specific antisera from rat and rabbit as a distinct band with a MW of ca. 65 or 80 kilodalton, where 26 kd of the fusion protein represent the GST protein and ca. 40 kd or 57 kd represent the C-terminal part of the p57 BDV-protein or the entire p57 BDV-protein.

EXAMPLE 3

Preparation of antisera and monoclonal antibodies

Polyvalent monospecific antiserum against the GST-p57/c fusion protein was obtained from a rabbit immunized subcutaneously with 1 mg GST-p57/c fusion protein in complete Freund's adjuvant (CFA). After 4 and 8 weeks the rabbit received a booster immunization with the same amount of antigen and was bled 1 week after the last immunization procedure. The serum was tested for its reactivity in indirect immunofluorescence assays on BDV-infected and uninfected MDCK cells as well as in Western blot analyses with the fusion protein.

Monoclonal antibodies were prepared using published procedures (Köhler & Milstein, 1975). Spleen cells were obtained from a Balb/c mouse immunized three times with 100 $\mu$g GST-p57/c in CFA.; the animal had a strong antibody reponse at the time of sacrifice. The supernatants of hybridomas were tested for BDV-specific antibodies by the indirect immunofluorescence assay (IFA) on persistently infected MDCK cells. Additionally, ELISA and Western blot analysis was performed. Hybridoma cells were cloned twice by picking single cells under a light microscope.

Polyvalent monospecific antiserum against the GST-p57/c fusion protein was obtained from a rabbit immunized subcutaneously with the GST-p57/c fusion protein as described above. This antisera was applied to persistently BDV-infected MDCK cells fixed in acetone (60 min at −20° C.) or 4% paraformaldehyde (PFA) for 30 min at room temperature. The monospecific antiserum recognized virus-specific proteins in acetone-fixed cells scattered throughout the cytoplasm of infected MDCK cells. When the cells were fixed with PFA in order to stain for surface antigen, intensive staining was found on the surface of BDV-infected MDCK cell. Furthermore, brain sections of experimentally BDV-infected rats were incubated with the monospecific and monoclonal anti-p57/c antisera. Viral antigen was detected mainly throughout the cytoplasm of infected neurons in the CNS of rats.

EXAMPLE 4

ELISA

Screening of antibody-producing hybridomas and sera from BDV-infected rats was performed using recombinant GST-p57/c protein and GST as the control protein.

Ninety-six well microtiter plates (Greiner, Germany) were coated overnight at 4° C. with 31 and 125 ng of recombinant GST-p57/c or GST protein per well in 50 $\mu$l of buffer (1.59 g $Na_2CO_3$, 2.93 g $NaHCO_3$ and 0.20 g $NaN_3$ in 1000 ml $H_2O$). Plates were washed three times with washing buffer (0.5% Tween-20 in PBS) and incubated 1 hour with blocking buffer (0.5% gelatin, 1% BSA, 0.1% Thimerosal in PBS with 0.5% Tween-20) at room temperature. The microtiter plate was washed three times with washing buffer and 2 fold dilutions of the sera were prepared in the blocking buffer. 50 $\mu$l of the respective sera diluted from 1:20 to 1:10240 was added to each well and incubated for 1 hour at room temperature. Plates were washed three times with washing buffer and biotin-conjugated rabbit anti-rat or anti-mouse IgG and IgM diluted 1:10 000 in blocking buffer were added to each well and incubated 1 hour at room temperature. After washing three times the plates were incubated with horseradish peroxidase conjugated to streptavidin (Amersham, Braunschweig), diluted 1:10 000 in blocking buffer for 1 hour at room temperature. After washing the plates three times, 200 $\mu$l of substrate solution was added to each well. The substrate solution consisted of 0.5 M $Na_2PO_4$, 0.1 M citric acid, 20 mg phenyldiamine and 20 ml 30% $H_2O_2$ in 50 ml $H_2O$. The plates were incubated for 5–10 min at room temperature and the reaction stopped by the addition of 50 $\mu$l sulphuric acid to each well. The absorbance at 492 nm was determined for each well using a microplate reader. Negative control wells without the primary antisera were used for calibration. The ELISA titer for each serum was defined as the endpoint dilution that yielded an optical density of 0.2. The results of this test using a convalescent and control rat serum are shown in FIG. 6.

In order to establish a specific and sensitive ELISA for the recombinant BDV p57/c protein, the optimal antigen concentration was determined by checkerboard titration of positive and negative rat sera versus the following antigen concentrations: 31, 62, 125, 250 ng/well. The optimal concentration with the greater linear response was 31 ng/well. The sensitivity of the ELISA system for the recombinant p57/c BDV-protein was established using sera from experimentally infected rats on days 40, 50 and 60 post infection (p.i.) known to be reactive by IFA (Titers ranging from 1:2280 to 1:5120) and Western blot analysis. All sera that has been found positive by these methods were also positive in the ELISA-system using the recombinant p57/c protein. The specificity was tested using sera from 5 noninfected rats and recombinant GST protein. Each ELISA proved to be highly specific for the detection of antibodies to the recombinant p57/c BDV-protein: at a dilution of 1:80 the noninfected rat sera had an OD-range from 0.026 to 0.051, the BDV-infected rat sera from 0.363 to 0.566. No nonspecific background was observed at dilutions 1:40 or higher.

EXAMPLE 5

Cloning and expression of the p9.5 BDV-gene

The open reading frame of the p9.5 BDV-protein was amplified from CDNA of the B8 clone [VandeWoude et al., (1990) Science 250, p. 1278–1281] and from a field isolate of BDV (horse) using the following primers:

```
3' Primer (anti-sense) GCGGAATTC TCATCATTCGATGCTGCTCCC (SEQ ID NO: 8)

5' Primer (sense): ATAGGATCC ATGAGTTCCGACCTCCGGC        (SEQ ID NO: 9)
```

The conditions for the PCR reaction were described in example 1.

The amplified product was purified from agarose gels and cloned into the plasmid vector pGEX-2T (Pharmacia, Freiburg, Germany; Nr. 27-4801-01) after the restriction sites were cleaved using the restriction enzymes BamHI and EcoRI (Promega, Madison, USA). The viral gene was fused to the Glutathione-S-transferase (GST) gene of *Schistosoma japonicum* controlled by the tac promotor. The expression plasmid was transformed into competent *E. coli* Sure™-cells. Recombinant plasmids were analyzed using restriction analysis and DNA-sequencing methods. The DNA sequence of the cloned fragment (pGEX-p9.5) from the field isolate is shown in FIG. 5.

EXAMPLE 6

Expression and purification of the p9.5 BDV-protein in *E. coli:*

100 ml of pGEX-p9.5 containing *E. coli* were grown overnight in LB-medium with 0.1 mg/ml ampicillin (Serva, Heidelberg). This overnight culture was diluted in 1 liter of LB-medium with ampicillin and grown to log phase for 2–4 hours. The expression of the GST-p9.5 fusion protein was induced with IPTG (0.1 mM; Promega, Heidelberg, Germany) for 4 hours. The bacteria were pelleted by centrifugation (5900 g, 10 min, 4° C.) and resuspended in PBS. The cells were lysed by sonication on ice and the cell debris pelleted by centrifugation (9800 g, 10 min, 4° C.). The sonicated fusion protein supernatant was added to an affinity matrix with glutathione (Glutathione Sepharose 4 B; Pharmacia, Nr. 27-4570-01). The purification of the GST-p9.5 fusion protein using Glutathione Sepharose 4B was done according to the manufacturer's protocol. The eluted fusion protein was dialyzed against 1×PBS for 24 hours at 4° C. The expression product was analyzed in SDS-PAGE and Immunoblot assays.

The expression of the virus-specific GST-p9.5 fusion protein by a recombinant pGEX-p.9.5 clone was analyzed by immunoblotting using *E.coli* lysates treated with and without IPTG. As a control an *E. coli* lysate transformed with the nonrecombinant pGEX-2T plasmid was used. The quality of the eluted fusion protein was analyzed by Western blot analyses using BDV-specific rat and rabbit antisera. The purified GST-p9.5 was easily detected by virus-specific antisera from rat and rabbit as a distinct band with a MW of ca. 35 kilodalton; 26 kd of the fusion protein represent the GST protein and ca. 9 kb represent the p9.5 BDV-protein.

EXAMPLE 7

SDS-PAGE, SDS-PAGE-Tricin and Western blot analysis 10 ml of the purified recombinant GST-p9.5 and GST proteins, uninfected and BDV-infected OligoTL cell lysates as well as uninfected and BDV-infected rat brain homogenates were suspended in Laemmli sample buffer (Laemmli, 1970), heated for 2 min at 100° C., and separated by sodium dodecyl sulfate-polyacrylamide gel electrophoresis (SDS-PAGE) on gels containing 12% polyacrylamide. The separated proteins were transferred to nitrocellulose membrane by electroblotting. Polyclonal antisera from rabbits and rats and monospecific rabbit anti-GST-p9.5 antisera were diluted 1:100 in PBS containing 0.5% Tween-80 and 5% BSA. Nitrocellulose strips were incubated overnight at 4° C. with the respective diluted antisera. After the strips were washed three times with PBS/0.5% Tween-20 (washing buffer) they were incubated with anti-species antibodies marked with biotin (Amersham, Braunschweig, Germany) in a dilution of 1:1000. After three washes with washing buffer the nitrocellulose strips were incubated with streptavidin conjugated horseradish peroxidase (Amersham, Braunschweig, Germany) diluted 1:2000 in washing buffer. Finally the strips were washed three times in PBS and stained in a solution of 0.5 mg/ml 4-chloro-1-naphthol, 20% (v/v) methanol and 0.4 ml/ml $H_2O_2$.

Tricin-SDS-PAGE gels were used for the separation of the affinity purified proteins; tricin allows the resolution of small proteins. Shortly thereafter, 12% acrylamide gels were prepared as described above. The anode buffer consisted of 0.2 M Tris (pH 8.9), the cathode buffer of 0.1 M Tris (pH8.25), 0.1 M Tricin and 0.1% SDS (Schägger & Jagow, 1987). The separated proteins of the Tricin-SDS-PAGE gel were further analyzed by immunoblot technique as described above.

EXAMPLE 8

Preparation of antisera

Polyvalent monospecific antiserum against the GST-p9.5 fusion protein was obtained from a rabbit immunized subcutaneously with 1 mg GST-p9.5 fusion protein in complete Freund's adjuvant (CFA). 4 and 8 weeks later the rabbit received booster immunizations with the same amount of antigen and was bled 1 week after the last immunization procedure. The sera were tested for their reactivity in indirect immunofluorescence assays on BDV-infected and uninfected MDCK cells as well as in Western blot analyses.

These antisera were applied to persistently BDV-infected MDCK cells fixed in acetone for 60 min at −20° C. The monospecific antiserum recognized virus-specific proteins mainly located in the nuclei of infected cells. This staining pattern was analogous to the reaction with monoclonal or monospecific antibodies specific for the p38 BDV-protein. Double immunofluorescence techniques using FITC and TRITC-labelled secondary antibodies revealed that the p9.5 BDV-protein colocalizes in the nucleus of infected cells with the p38 BDV-protein, the putative nucleoprotein of BDV. Furthermore, brain sections of experimentally BDV-infected rats were incubated with the monospecific anti-GST-p9.5 rabbit antiserum. Viral antigen was detected in the nucleus and cytoplasm of infected neurons in the CNS of rats.

EXAMPLE 9

Antibody-mediated affinity chromatography

The procedure has been described by Haas et al. [J. Gen. Virol. 67 (1986), p. 235–241]. In brief, sepharose CL-6B was treated with phoroglucinol and epichlorhydrin, activated with cyanogen bromide dissolved in acetonitrile, and conjugated with the gamma globulin fraction of the monospecific rabbit anti-GST-p9.5 serum at 4° C. overnight. About 300 mg of protein were used per 10 ml of packed, activated sepharose. The column with the antibody-coated sepharose was equilibrated with PBS. After the application of the tissue or cell extracts, the column was washed extensively with PBS/1M NaCl and finally with Tris/NaCl (TN) buffer only. The material retained on the immunosorbent was eluted with PBS/1M $NaClO_4$. The eluate was concentrated by centrifugation dialysis using Ultrafree-MC 10 kD-filters (Millipore, Germany) at 4° C.

In order to purify the p9.5 BDV-protein from BDV-infected cells, BDV-infected OligoTL cells were washed with PBS and scraped from the bottom of culture dishes. The cell suspension was then washed and resuspended with PBS and sonicated three times for 10 seconds. The cell homogenate was centrifuged (5000 g, 10 min, 4° C.) and the supernatant applied to the affinity column with anti-p9.5 antibodies. The column was washed and eluted as described above. Similarly, a 10% homogenate of a BDV-infected rat brain in TN-buffer was stirred for 1 hour at room temperature after the addition of 1% Triton X-100 and 0.5% deoxycholate. The homogenate was centrifuged for 2 hours at 30 000 r.p.m. in a Beckman 45 Ti rotor to remove cell debris. The supernatant was applied to the affinity column and processed as described above.

The antibody-mediated affinity purification procedure with both antigen sources resulted clearly in the isolation of a virus-specific protein with a MW of approximately 9.5 kD; the 9.5 BDV-protein does not contain carbohydrate side chains as analyzed using a DIG glycon detection kit.

EXAMPLE 10

ELISA

Screening of antibody-producing hybridomas and sera from BDV-infected rats were performed using recombinant GST-p9.5 protein and GST as the control protein.

Ninety-six well microtiter plates (Greiner, Germany) were coated overnight at 4° C. with 31 and 125 ng of recombinant GST-p9.5 or GST protein per well in 50 $\mu$l of buffer (1.59 g $Na_2CO_3$, 2.93 g $NaHCO_3$ and 0.20 g $NaN_3$ in 1000 ml $H_2O$). Plates were washed three times with washing buffer (0.5% Tween-20 in PBS) and incubated 1 hour with blocking buffer (0.5% gelatin, 1% BSA, 0.1% Thimerosal in PBS with 0.5% Tween-20) at room temperature. The microtiter plate was washed three times with washing buffer and 2 fold dilutions of the sera were prepared in the blocking buffer. 50 $\mu$l of the respective sera diluted from 1:20 to 1:10240 were added to each well and incubated for 1 hour at room temperature. Plates were washed three times with washing buffer and biotin-conjugated rabbit anti-rat or anti-mouse IgG and IgM diluted 1:10 000 in blocking buffer were added to each well and incubated 1 hour at room temperature. After washing three times the plates were incubated with horseradish peroxidase conjugated to streptavidin (Amersham, Braunschweig), diluted 1:10 000 in blocking buffer for 1 hour at room temperature. After washing the plates three times, 200 pl of substrate solution was added to each well. The substrate solution consisted of 0.5 M $Na_2PO_4$, 0.1 M citric acid, 20 mg phenyldiamine and 20 ml 30% $H_2O_2$ in 50 ml $H_2O$. The plates were incubated for 5–10 min at room temperature and the reaction stopped by the addition of 50 $\mu$l sulphuric acid to each well. The absorbance at 492 nm was determined for each well using a microplate reader. Negative control wells without the primary antisera were used for calibration. The ELISA titer for each serum was defined as the endpoint dilution that yielded an optical density of 0.2. The results of this test using a convalescent and control rat serum are shown in FIG. 7.

In order to establish a specific and sensitive ELISA for the recombinant BDV p9.5 protein, the optimal antigen concentration was determined by checkerboard titration of positive and negative rat sera versus the following antigen concentrations: 31, 62, 125, 250 ng/well. The optimal concentration with the most linear response was 31 ng/well. The sensitivity of the ELISA system for the recombinant p9.5 BDV-protein was established using sera from experimentally infected rats on days 40, 50 and 60 post infection (p.i.) known to be reactive by IFA (Titers ranging from 1:2280 to 1:5120) and Western blot analysis. All sera that has been found positive by these methods were also positive in the ELISA-system using the recombinant p9.5 protein. The specificity was tested using sera from 5 noninfected rats and recombinant GST protein. Each ELISA proved to be highly specific for the detection of antibodies to the recombinant p57/c BDV-protein: at a dilution of 1:80 the noninfected rat sera had an OD-range from 0.026 to 0.051, the BDV-infected rat sera from 0.363 to 0.566. No nonspecific background was observed at dilutions 1:40 or higher.

I claim:

1. A method of detecting antibody indicative of infection by Borna disease virus, comprising contacting a sample with a polypeptide comprising the sequence of the C-terminal region of p57, under conditions for antibody binding, and detecting antibodies bound to said polypeptide.

2. The method of claim 1, wherein the polypeptide comprises SEQ ID NO:3.

3. The method of claim 1, wherein the sample is serum.

4. The method of claim 1, wherein the detecting is performed using ELISA, Western blot, RIA, or dot blot.

5. A test kit useful in determining an antibody directed against Borna disease virus, comprising a polypeptide comprising the sequence of the C-terminal region of p57 and a labeled substance specific for complexes of said antibody and said polypeptide.

6. The test kit of claim 5, wherein the polypeptide comprises SEQ ID NO:3.

7. The test kit of claim 6, wherein the kit comprises the components for performing an ELISA, Western blot, RIA, or dot blot test.

8. The test kit of claim 6, wherein the labeled substance is a labeled antibody which specifically binds the antibody to be determined.

9. The test kit of claim 8, wherein the label is an enzyme which can catalyze a reaction resulting in a colored end product.

10. An isolated polypeptide comprising the sequence of SEQ ID NO. 1 or SEQ ID NO. 3.

11. An immunogenic composition comprising the polypeptide of claim 10.

12. An isolated polypeptide consisting of the amino acid sequence set forth in SEQ ID NO: 3.

13. A method for inducing antibodies to a Borna Disease Virus in a subject comprising the step of immunizing the subject with a composition comprising a polypeptide consisting of the sequence set forth in SEQ ID NO: 3 fused to a non-BDV polypeptide in an amount sufficient to induce antibody production in said subject.

* * * * *

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
(A) LENGTH: 503 amino acids
(B) TYPE: amino acid
(C) STRANDEDNESS: single
(D) TOPOLOGY: linear (ii) MOLECULE TYPE: Protein (v) FRAGMENT TYPE: internal (xi) SEQUENCE DESCRIPTION: SEQ ID NO: 1:

```
Met Gln Pro Ser Met Ser Phe Leu Ile Gly Phe Gly Thr Leu Val Leu
  1               5                  10                  15
```

-continued

```
Ala Leu Ser Ala Arg Thr Phe Asp Leu Gln Gly Leu Ser Cys Asn Thr
            20                  25                  30

Asp Ser Thr Pro Gly Leu Ile Asp Leu Glu Ile Arg Arg Leu Cys His
        35                  40                  45

Thr Pro Thr Glu Asn Val Ile Ser Cys Glu Val Ser Tyr Leu Asn His
    50                  55                  60

Thr Thr Ile Ser Leu Pro Ala Val His Thr Ser Cys Leu Lys Tyr His
65                  70                  75                  80

Cys Lys Thr Tyr Trp Gly Phe Phe Gly Ser Tyr Ser Ala Asp Arg Ile
                85                  90                  95

Ile Asn Arg Tyr Thr Gly Thr Val Lys Gly Cys Leu Asn Asn Ser Ala
            100                 105                 110

Pro Glu Asp Pro Phe Glu Cys Asn Trp Phe Tyr Cys Cys Ser Ala Ile
        115                 120                 125

Thr Thr Glu Ile Cys Arg Cys Ser Ile Thr Asn Val Thr Val Ala Val
    130                 135                 140

Gln Thr Phe Pro Pro Phe Met Tyr Cys Ser Phe Ala Asp Cys Ser Thr
145                 150                 155                 160

Val Ser Gln Gln Glu Leu Glu Ser Gly Lys Ala Met Leu Ser Asp Gly
                165                 170                 175

Ser Thr Leu Thr Tyr Thr Pro Tyr Ile Leu Gln Ser Glu Val Val Asn
            180                 185                 190

Arg Thr Leu Asn Gly Thr Ile Leu Cys Asn Ser Ser Ser Lys Ile Val
        195                 200                 205

Ser Phe Asp Glu Phe Arg Arg Ser Tyr Ser Leu Thr Asn Gly Ser Tyr
    210                 215                 220

Gln Ser Ser Ser Ile Asn Val Thr Cys Ala Asn Tyr Thr Ser Ser Cys
225                 230                 235                 240

Arg Pro Arg Leu Lys Arg Arg Arg Arg Asp Thr Gln Gln Ile Glu Tyr
                245                 250                 255

Leu Val His Lys Leu Arg Pro Thr Leu Lys Asp Ala Trp Glu Asp Cys
            260                 265                 270

Glu Ile Leu Gln Ser Leu Leu Leu Gly Val Phe Gly Thr Gly Ile Ala
        275                 280                 285

Ser Ala Ser Gln Phe Leu Arg Gly Trp Leu Asn His Pro Asp Ile Val
    290                 295                 300

Gly Tyr Ile Val Asn Gly Ile Gly Val Val Trp Gln Cys His Arg Val
305                 310                 315                 320

Asn Val Thr Phe Met Ala Trp Asn Glu Ser Thr Tyr Tyr Pro Pro Val
                325                 330                 335

Asp Tyr Asn Gly Arg Lys Tyr Phe Leu Asn Asp Glu Gly Arg Leu Gln
            340                 345                 350

Thr Asn Thr Pro Glu Ala Arg Pro Gly Leu Lys Arg Val Met Trp Phe
        355                 360                 365

Gly Arg Tyr Phe Leu Gly Thr Val Gly Ser Gly Val Lys Pro Arg Arg
    370                 375                 380

Ile Arg Tyr Asn Lys Thr Ser Arg Asp Tyr His Leu Glu Glu Phe Glu
385                 390                 395                 400

Ala Ser Leu Asn Met Thr Pro Gln Thr Ser Ile Ala Ser Gly His Glu
                405                 410                 415

Thr Asp Pro Ile Asn His Ala Tyr Gly Thr Gln Ala Asp Leu Leu Pro
            420                 425                 430

Tyr Thr Arg Ser Ser Asn Ile Thr Ser Thr Asp Thr Gly Ser Gly Trp
        435                 440                 445
```

```
Val His Ile Gly Leu Pro Ser Phe Ala Phe Leu Asn Pro Leu Gly Trp
    450                 455                 460

Leu Arg Asp Leu Leu Ala Trp Ala Ala Trp Leu Gly Gly Val Leu Tyr
465                 470                 475                 480

Leu Ile Ser Leu Cys Val Ser Leu Pro Ala Ser Phe Ala Arg Arg Arg
                485                 490                 495

Arg Leu Ala Arg Trp Gln Glu
            500
```

(2) INFORMATION FOR SEQ ID NO: 2:

(i) SEQUENCE CHARACTERISTICS:
(A) LENGTH: 87 amino acids
(B) TYPE: amino acid
(C) STRANDEDNESS: single
(D) TOPOLOGY: linear (ii) MOLECULE TYPE: Protein (v) FRAGMENT TYPE: internal (xi) SEQUENCE DESCRIPTION: SEQ ID NO: 2:

```
Met Ser Ser Asp Leu Arg Leu Thr Leu Leu Glu Leu Val Arg Arg Leu
  1               5                  10                  15

Asn Gly Asn Ala Thr Ile Glu Ser Gly Arg Leu Pro Gly Gly Arg Arg
            20                  25                  30

Arg Ser Pro Asp Thr Thr Thr Gly Thr Ile Gly Val Ala Lys Thr Thr
        35                  40                  45

Glu Asp Pro Lys Glu Cys Ile Asp Pro Thr Ser Arg Pro Ala Pro Glu
    50                  55                  60

Gly Pro Gln Glu Glu Pro Leu His Asp Leu Arg Pro Arg Pro Ala Asn
 65                  70                  75                  80

Arg Lys Gly Ala Ala Val Glu
                 85
```

(2) INFORMATION FOR SEQ ID NO: 3:

(i) SEQUENCE CHARACTERISTICS:
(A) LENGTH: 353 amino acids
(B) TYPE: amino acid
(C) STRANDEDNESS: single
(D) TOPOLOGY: linear (ii) MOLECULE TYPE: Peptide (v) FRAGMENT TYPE: internal (xi) SEQUENCE DESCRIPTION: SEQ ID NO: 3:

```
Met Tyr Cys Ser Phe Ala Asp Cys Ser Thr Val Ser Gln Gln Glu Leu
  1               5                  10                  15

Glu Ser Gly Lys Ala Met Leu Ser Asp Gly Ser Thr Leu Thr Tyr Thr
            20                  25                  30

Pro Tyr Ile Leu Gln Ser Glu Val Val Asn Arg Thr Leu Asn Gly Thr
        35                  40                  45

Ile Leu Cys Asn Ser Ser Ser Lys Ile Val Ser Phe Asp Glu Phe Arg
    50                  55                  60

Arg Ser Tyr Ser Leu Thr Asn Gly Ser Tyr Gln Ser Ser Ser Ile Asn
 65                  70                  75                  80

Val Thr Cys Ala Asn Tyr Thr Ser Ser Cys Arg Pro Arg Leu Lys Arg
                 85                  90                  95

Arg Arg Arg Asp Thr Gln Gln Ile Glu Tyr Leu Val His Lys Leu Arg
```

-continued

```
            100                 105                 110

Pro Thr Leu Lys Asp Ala Trp Glu Asp Cys Glu Ile Leu Gln Ser Leu
        115                 120                 125

Leu Leu Gly Val Phe Gly Thr Gly Ile Ala Ser Ala Ser Gln Phe Leu
    130                 135                 140

Arg Gly Trp Leu Asn His Pro Asp Ile Val Gly Tyr Ile Val Asn Gly
145                 150                 155                 160

Ile Gly Val Val Trp Gln Cys His Arg Val Asn Val Thr Phe Met Ala
                165                 170                 175

Trp Asn Glu Ser Thr Tyr Tyr Pro Pro Val Asp Tyr Asn Gly Arg Lys
            180                 185                 190

Tyr Phe Leu Asn Asp Glu Gly Arg Leu Gln Thr Asn Thr Pro Glu Ala
        195                 200                 205

Arg Pro Gly Leu Lys Arg Val Met Trp Phe Gly Arg Tyr Phe Leu Gly
    210                 215                 220

Thr Val Gly Ser Gly Val Lys Pro Arg Arg Ile Arg Tyr Asn Lys Thr
225                 230                 235                 240

Ser Arg Asp Tyr His Leu Glu Glu Phe Glu Ala Ser Leu Asn Met Thr
                245                 250                 255

Pro Gln Thr Ser Ile Ala Ser Gly His Glu Thr Asp Pro Ile Asn His
            260                 265                 270

Ala Tyr Gly Thr Gln Ala Asp Leu Leu Pro Tyr Thr Arg Ser Ser Asn
        275                 280                 285

Ile Thr Ser Thr Asp Thr Gly Ser Gly Trp Val His Ile Gly Leu Pro
    290                 295                 300

Ser Phe Ala Phe Leu Asn Pro Leu Gly Trp Leu Arg Asp Leu Leu Ala
305                 310                 315                 320

Trp Ala Ala Trp Leu Gly Gly Val Leu Tyr Leu Ile Ser Leu Cys Val
                325                 330                 335

Ser Leu Pro Ala Ser Phe Ala Arg Arg Arg Arg Leu Ala Arg Trp Gln
            340                 345                 350

Glu
```

(2) INFORMATION FOR SEQ ID NO: 4:

(i) SEQUENCE CHARACTERISTICS:
- (A) LENGTH: 1512 base pairs
- (B) TYPE: nucleic acid
- (C) STRANDEDNESS: single
- (D) TOPOLOGY: linear (ii) MOLECULE TYPE: Genomic DNA (xi) SEQUENCE DESCRIPTION: SEQ ID NO: 4:

```
ATGCAGCCTT CAATGTCTTT TCTTATCGGC TTCGGAACAT TGGTGTTGGC CCTCTCGGCC     60

CGGACATTCG ATCTTCAGGG CCTTAGTTGC AATACTGACT CCACTCCTGG ACTGATCGAC    120

CTGGAGATAA GGCGACTTTG CCACACCCCA ACGGAAAATG TCATTTCATG CGAGGTTAGT    180

TATCTTAACC ACACGACTAT TAGCCTCCCG GCAGTCCACA CATCATGCCT CAAGTACCAC    240

TGCAAAACCT ATTGGGGATT CTTTGGTAGT TACAGCGCTG ACCGAATCAT CAATCGGTAC    300

ACTGGTACTG TTAAGGGTTG TTTAAACAAC TCAGCACCAG AAGACCCCTT CGAGTGCAAC    360

TGGTTCTACT GCTGCTCGGC GATTACAACA GAAATCTGCC GATGCTCTAT TACAAATGTC    420

ACAGTGGCTG TACAAACATT CCCACCGTTT ATGTACTGCA GCTTTGCGGA CTGTAGCACC    480

GTGAGTCAGC AGGAGCTAGA GAGTGGAAAG GCAATGCTGA GCGATGGCAG CACATTAACT    540
```

-continued

```
TATACCCCTT ATATCTTACA GTCAGAAGTC GTGAACAGAA CCCTTAATGG GACCATACTC    600

TGCAACTCAT CCTCCAAGAT AGTTTCCTTT GATGAATTTA GGCGTTCATA CTCCCTAACG    660

AATGGTAGTT ACCAGAGCTC ATCAATCAAT GTGACGTGTG CAAACTACAC GTCGTCCTGC    720

CGGCCCAGGT TGAAAAGGCG GCGTAGGGAC ACCCAGCAGA TTGAGTATCT AGTTCACAAG    780

CTTAGGCCCA CACTGAAAGA TGCATGGGAG GACTGTGAGA TCCTCCAGTC TCTGCTCCTA    840

GGGGTGTTTG GTACTGGGAT CGCAAGTGCT TCTCAATTTT TGAGGGGCTG GCTCAACCAC    900

CCTGACATCG TCGGGTATAT AGTTAATGGA ATTGGGGTTG TCTGGCAATG CCATCGTGTT    960

AATGTCACAT TCATGGCGTG GAATGAGTCC ACATATTACC CTCCAGTAGA TTACAATGGG   1020

CGGAAGTACT TTCTGAATGA TGAGGGGAGG CTACAAACAA ACACCCCCGA GGCGAGGCCA   1080

GGGCTAAAGC GGGTCATGTG GTTCGGTAGG TACTTCCTAG GGACAGTAGG GTCTGGGGTG   1140

AAACCGAGGA GGATTCGGTA CAATAAGACT TCACGTGACT ACCACCTAGA GGAGTTTGAG   1200

GCAAGTCTCA ACATGACCCC CCAGACCAGT ATCGCTTCAG GTCATGAGAC AGACCCCATA   1260

AATCATGCCT ACGGAACGCA GGCTGATCTC CTTCCATACA CCAGGTCTAG TAATATAACG   1320

TCTACAGATA CAGGCTCAGG CTGGGTGCAC ATCGGCCTAC CCTCATTTGC CTTCCTCAAT   1380

CCCCTCGGGT GGCTCAGGGA CTTACTTGCA TGGGCGGCCT GGTTGGGTGG GGTCCTATAC   1440

TTAATAAGTC TTTGTGTTTC CTTACCAGCC TCCTTCGCGA GGAGGAGACG CCTCGCGCGG   1500

TGGCAGGAAT AA                                                       1512
```

(2) INFORMATION FOR SEQ ID NO: 5:

(i) SEQUENCE CHARACTERISTICS:
(A) LENGTH: 264 base pairs
(B) TYPE: nucleic acid
(C) STRANDEDNESS: single
(D) TOPOLOGY: linear (ii) MOLECULE TYPE: Genomic DNA (xi) SEQUENCE DESCRIPTION: SEQ ID NO: 5:

```
ATGAGTTCCG ACCTCCGGCT GACATTGCTT GAACTAGTCA GGAGGCTCAA TGGCAACGCG     60

ACCATCGAGT CTGGTCGACT CCCTGGAGGA CGAAGAAGAT CCCCAGACAC TACGACGGGA    120

ACGATCGGGG TCACCAAGGC CACGGAAGAT CCCAAGGAAT GCATTGACCC AACCAGTCGA    180

CCAGCTCCTG AAGGACCTCA GGAAGAACCC CTCCATGATC TCAGACCCAG ACCAGCGAAC    240

CGGAAGGGAG CAGCTGTCGA ATGA                                           264
```

(2) INFORMATION FOR SEQ ID NO: 6:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: Genomic DNA (xi) SEQUENCE DESCRIPTION: SEQ ID NO: 6:

```
GTAGAATTCT TATTCCTGCC ACCGGCCGAG GCGTC                                35
```

(2) INFORMATION FOR SEQ ID NO: 7:

(i) SEQUENCE CHARACTERISTICS:
(A) LENGTH: 35 base pairs
(B) TYPE: nucleic acid
(C) STRANDEDNESS: single
(D) TOPOLOGY: linear -continued

```
    (ii) MOLECULE TYPE: Genomic DNA

    (xi) SEQUENCE DESCRIPTION: SEQ ID NO:  7:

GATGGATCCA TGTACTGCAG TTTCGCGGAC TGTAG                                35


(2) INFORMATION FOR SEQ ID NO:  8:

     (i) SEQUENCE CHARACTERISTICS:
          (A) LENGTH: 31 base pairs
          (B) TYPE: nucleic acid
          (C) STRANDEDNESS: single
          (D) TOPOLOGY: linear

    (ii) MOLECULE TYPE: Genomic DNA

    (xi) SEQUENCE DESCRIPTION: SEQ ID NO:  8:

GCGGAATTCT CATCATTCGA TAGCTGCTCC C                                    31


(2) INFORMATION FOR SEQ ID NO:  9:

     (i) SEQUENCE CHARACTERISTICS:
          (A) LENGTH: 28 base pairs
          (B) TYPE: nucleic acid
          (C) STRANDEDNESS: single
          (D) TOPOLOGY: linear

    (ii) MOLECULE TYPE: Genomic DNA

    (xi) SEQUENCE DESCRIPTION: SEQ ID NO:  9:

ATAGGATCCA TGAGTTCCGA CCTCCGGC                                        28
```